US00PP12437P2

(12) United States Plant Patent
Noodelijk

(10) Patent No.: US PP12,437 P2
(45) Date of Patent: Mar. 5, 2002

(54) CHRYSANTHEMUM PLANT NAMED 'VIRUNGA'

(75) Inventor: Robert Noodelijk, Woubrugge (NL)

(73) Assignee: Chrysanthemum Breeders Association, N.V. (NL)

( * ) Notice: Subject to any disclaimer, the term of this patent is extended or adjusted under 35 U.S.C. 154(b) by 0 days.

(21) Appl. No.: 09/561,934

(22) Filed: May 1, 2000

(51) Int. Cl.[7] ..... A01H 5/00
(52) U.S. Cl. ..... Plt./296
(58) Field of Search ..... Plt./296

*Primary Examiner*—Bruce R. Campell
*Assistant Examiner*—Annette H. Para
(74) *Attorney, Agent, or Firm*—Parkhurst & Wendell, L.L.P.

(57) ABSTRACT

A Chrysanthemum plant named 'Virunga' characterized by its Large sized blooms with Yellow-Orange ray-florets and Yellow-Green disc florets.

2 Drawing Sheets

RELATED CULTIVARS

'Virunga' is related to Yellow 'Virunga' (copending U.S. application Ser. No. 09/561,933). Yellow 'Virunga' is a color mutant from 'Virunga'.

BACKGROUND OF THE INVENTION

'Virunga' is a product of a breeding-program which had the objective of creating new chrysanthemum cultivars with a daisy type flower, a 7 week response and a medium plant height. The new plant of the present invention comprises a new and distinct cultivar of Chrysanthemum plant. 'Virunga' is a seedling from a cross in a breeding program maintained under the control of inventor. The female parent is #94.005—unpatented—, an unamed seedling not available to inventor for description. The male parent is unknown, being a mixed pollation of a group of male parents. The new and distinct cultivar was discovered and selected as a flowering plant within the progeny of the stated cross by Rob Noodelijk in a controlled environment (greenhouse) in Rijsenhout Holland in May 1996. The first act of asexual reproduction of 'Virunga' was accomplished when vegetative cuttings were taken from the initial selection in August 1996 in a controlled environment in Rijsenhout Holland.

SUMMARY OF THE INVENTION

The present invention is a new and distinct variety of chrysanthemum bearing large sized blooms with yellow-orange ray-florets and yellow-green disc florets.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
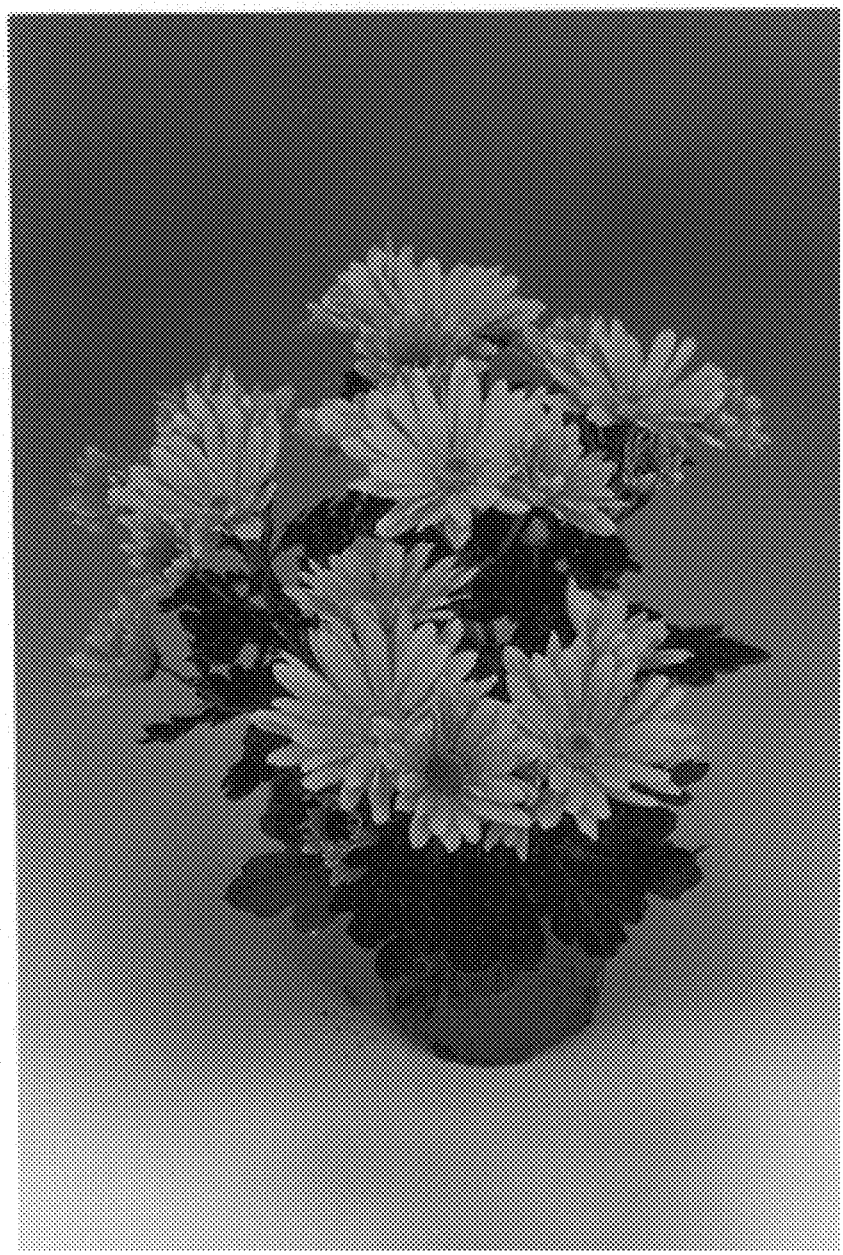
FIG. 1 shows a plant of the cultivar in full bloom.
Figure 2:
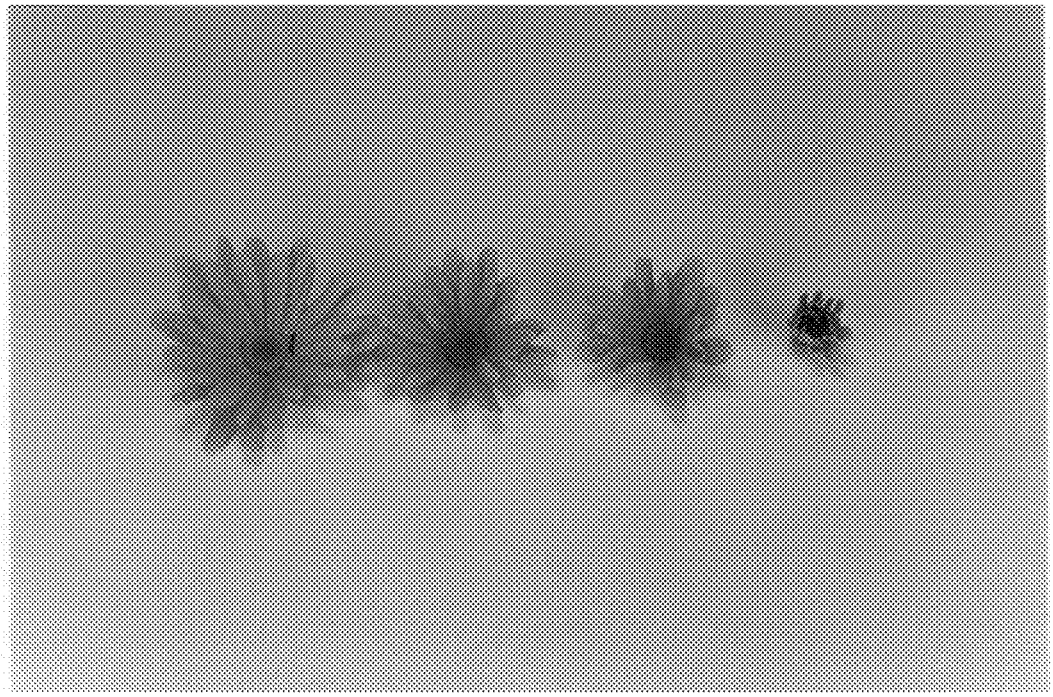
FIG. 2 shows the various stages of bloom of the new cultivar.
Figure 3:
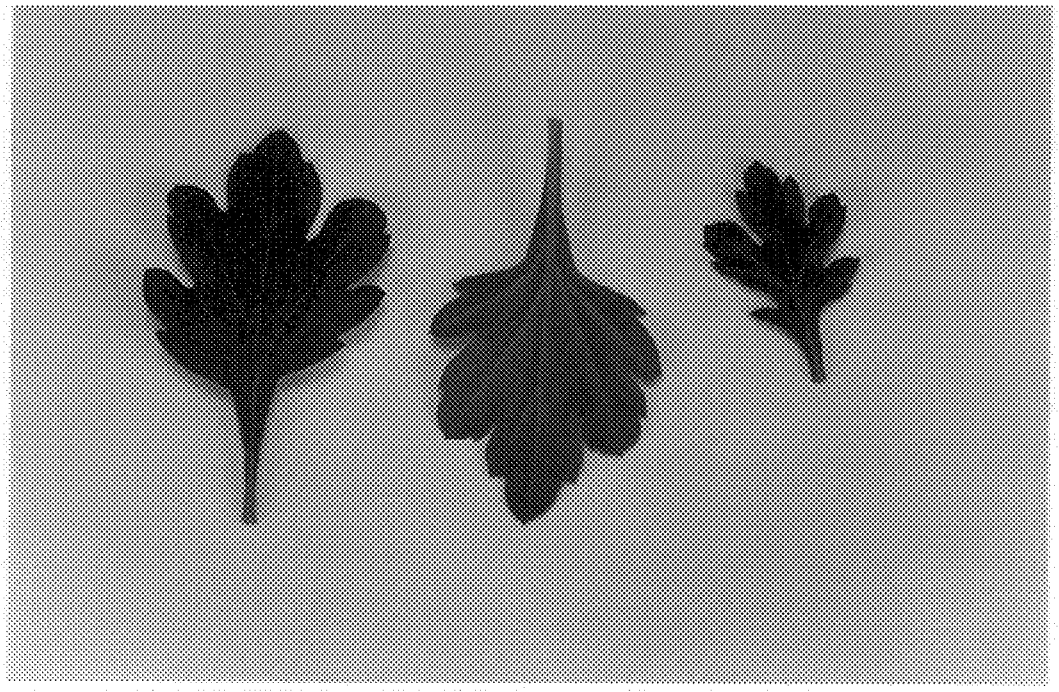
FIG. 3 shows the various stages of foliage and petiole of the new cultivar.

This new variety of chrysanthemum is of the botanical classification *dendranthema grandiflora*. The observations and measurements were gathered from plants grown in a greenhouse in Rijsenhout Holland in a photo-periodic controlled crop under conditions generally used in commercial practice. The greenhouse temperatures during this crop were at day-time between 18° C. and 25° C. and at night 20° C. The photo-periodic response time in this crop was 53 days after an average of eight long days. After this long day period to flowering growth retardants were applied 6 times in an average dose of 1.5 gram/liter water. No tests were done on disease or insect resistance or susceptibility. This new variety produces large sized blooms with yellow-orange ray-florets and yellow-green disc-florets blooming on the plant for 5 weeks. This new variety of chrysanthemum has been found to retain its distinctive characteristics throughout successive propagations however the phenotype may vary significantly with variations in environment such as light intensity and temperature. To show the phenotype as described 'Virunga' can be planted without assimilation lightning (high pressure sodium lamps) between week 50 and week 40 of the next year under greenhouse conditions in Holland. With assimilation lightning (minimum level 2500 lux) it can be planted year round under greenhouse conditions in Holland.

From the cultivars known to inventor the most similar existing cultivar in comparison to 'Virunga' is Yellow 'Virunga'. When Yellow 'Virunga' and 'Virunga' are being compared the following difference is noticed: The differences of Yellow 'Virunga' and 'Virunga' is the ray-floret color. 'Virunga' is yellow-orange, Yellow 'Virunga' is clear yellow.

From other commercial available varieties known to the inventor 'Orange Blush' (U.S. Plant Pat. No. 9,451) is most similar. The most obvious differences are (1) Flower form and color. The color of 'Virunga' is deeper orange, the ray-florets are less reflexing. (2) Vigor. 'Virunga' is more vigorous than 'Orange Blush'.

The following is a description of the plant and characteristics that distinguish 'Virunga' as a new and distinct variety.

The color designations are taken from the plant itself. Accordingly, any discrepancies between the color designations and the colors depicted in the photographs are due to photographic tolerances. The color chart used in this description is: The Royal Horticultural Society color chart, edition 1995.

TABLE 1

| Botanical Description of CULTIVAR 'VIRUNGA' | |
|---|---|
| Bud | |
| Size | Large; cross-section 1.0 cm, height 1.0 cm |
| Outside Color | Yellow-orange 22 C |
| Involucral bracts | 2 rows, length 7 mm, width 3 mm |
| Involucral bracts among disc-florets | Not present |
| Involucral bracts color | Yellow-green 146 D |
| Bloom | |
| Type | Daisy |
| Height | Flat |
| Size | Large |
| Fully Expanded | 6.5–7.0 cm. |
| Number of blooms per branch | Approx. 4 blooms per branch |
| Performance on the plant | 5 weeks |
| Seeds | Not produced |
| Fragrance | Typical chrysanthemum |
| Color | |
| Center of the flow (disc-florets) | Immature yellow-green 144 A<br>Mature yellow-orange 15 C |
| Color of upper surface of the ray-florets | Yellow-orange 22 A with a pattern of Yellow 15 A, Yellow 15 A at the tips |
| Color of the lower surface of the ray-florets | Yellow-orange 18 A |
| Tonality from Distance | A pot mum with pale orange flowers and a green disc |
| Discoloration to color | Yellow-orange 22 B |
| Ray florets | |
| Texture | Upper and under side smooth. |
| Number | 27–30 |
| Cross-section | Concave |
| Longitudinal axis of majority | Reflexing |
| Length of corolla tube | Short |
| Ray-floret length | 3.0–3.2 cm. |
| Ray-floret width | 0.8–1.0 cm. |
| Ratio length/width | Medium |
| Shape of tip | Pointed |
| Disc florets | |
| Disc diameter | 1.2–1.5 cm. |
| Distribution of disc florets | Numerous clearly visible at all stages of flowering. |
| Shape | Tubular |
| Color | Yellow-green 144 A |
| Receptacle shape | Conical raised |
| Reproductive Organs | |
| Stamen (present in disc florets only) | Yellow-green, thick, 4 mm. |
| Number of stamen | Grown together as one |
| Stamen color | Yellow-green 144 C |
| Pollen | Present at mature stage |
| Pollen color | Yellow-orange 12 A |
| Styles (present in both ray and disc florets) | Yellow-green, thin |
| Style color | Yellow-green 144 C |
| Style Length | 5 mm. |

TABLE 1-continued

| Botanical Description of CULTIVAR 'VIRUNGA' | |
|---|---|
| Stigmas | Yellow-green |
| Stigma Width | 2 mm. |
| Ovaries | Enclosed in calyx |
| Plant | |
| Form | A pot mum meant for indoor use |
| Growth habit | Spreading |
| Growth rate | Rapid |
| Height | 24–26 cm. |
| Width | 26–28 cm. |
| Stem Color | Yellow-green 146 D |
| Stem Strength | Medium to strong |
| Stem Brittleness | Absent |
| Stem Anthocyanin Coloration | Absent |
| Length of lateral branch | From top to bottom 12–13 cm |
| Lateral branch color | Yellow-green 146 D |
| Lateral branch, attachment | Weak |
| Branching (average number of lateral branches) | Poor with 3 breaks after pinching |
| Peduncle length | 3.0–4.5 cm. |
| Peduncle color | Yellow-green 146 D |
| Flowering | 53 Days |
| Response (photo-periodic controlled crop, not natural season | |
| Foliage | |
| Color | Upper side green 137 A<br>Under side green 147 B |
| Size | Medium; length 7.0 cm, width 5.0 cm |
| Quantity (number per lateral branch) | 6–8 |
| Shape | Ovate |
| Texture upper side | Glabrous |
| Texture under side | Pubescent |
| Venation arrangement | Palmate |
| Shape of the margin | Serrated |
| Shape of Base of Sinus Between Lateral Lobes | Round |
| Margin of Sinus Between Lateral Lobes | Converging |
| Shape of Base | Rounded (sometimes asymmetric) |
| Apex | Mucronate |

TABLE 2

| Differences with the comparison varieties | | | |
|---|---|---|---|
| | 'VIRUNGA' | 'YELLOW VIRUNGA' | 'ORANGE BLUSH' |
| Ray-floret color | Yellow-orange 22 A | Yellow 3 A | Yellow-orange 20 B |
| Growth rate | rapid | rapid | Slow |

I claim:

1. A new and distinct variety of chrysanthemum plant as described and illustrated.

* * * * *